United States Patent [19]

Carmosin et al.

[11] Patent Number: 4,800,207
[45] Date of Patent: Jan. 24, 1989

[54] HEXAHYDROPYRROLIZINE COMPOUNDS USEFUL AS ANALGESICS

[75] Inventors: Richard J. Carmosin, Quakertown; John R. Carson, Norristown, both of Pa.

[73] Assignee: McNeilab, Inc., Spring House, Pa.

[21] Appl. No.: 115,960

[22] Filed: Nov. 2, 1987

[51] Int. Cl.⁴ .................. C07D 487/02; A61K 31/40
[52] U.S. Cl. ..................................... 514/413; 548/453
[58] Field of Search ..................... 548/453; 514/413

[56] References Cited

U.S. PATENT DOCUMENTS

| | | | |
|---|---|---|---|
| 4,582,836 | 4/1986 | Carmosin et al. | 548/453 |
| 4,683,239 | 7/1987 | Carmosin et al. | 548/453 |
| 4,689,329 | 8/1987 | Carmosin et al. | 548/453 |
| 4,716,172 | 12/1987 | Carmosin et al. | 548/453 |

OTHER PUBLICATIONS

Chemical Abstracts at vol. 52, pp. 18409b to 18410d (1958).
"Studies on Psychotropic Agents . . . ", Chem. Pharm. Bull. vol. 27, Nagai et al., No. 5, pp. 1159–1168 (1979).
J. Heterocyclic Chem., vol. 14, Stetter et al., pp. 573–581, Jun. 1977.
J. Org. Chem., M. G. Reinecke et al., vol. 31, pp. 4215–4220 (1966).
Yakugaku Zasshi, I. Murakoshi, vol. 78, pp. 598–601 (1958).
Helv. Chim. Acta, H. Faber et al., vol. 56, pp. 2882–2884 (1973).

Primary Examiner—John M. Ford
Assistant Examiner—Robert C. Whittenbaugh
Attorney, Agent, or Firm—David J. Levy

[57] ABSTRACT

Hexahydropyrrolizines of the formula (I):

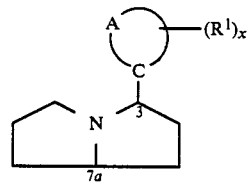

wherein
A is a 3-7 carbon or hetero-containing ring,
$R^1$ is a substituent, and
x is 0-3.

Also, pharmaceutical compositions for treating pain and methods for synthesis and use as well as novel intermediates in the synthesis.

15 Claims, No Drawings

HEXAHYDROPYRROLIZINE COMPOUNDS USEFUL AS ANALGESICS

The present invention comprises certain hexahydropyrrolizine compounds including acid addition salts thereof, methods for their preparation and use, pharmaceutical compositions and intermediates used in their synthesis. 3-Aryloctahydroindolizines are disclosed by I. Murakoshi in Yakugaku Zasshi, 78, pages 594–7 (1958) which appears in Chemical Abstracts at Volume 52, pages 18409b to 18410d (1958); by Y. Nagai et al in Chem. Pharm. Bull., 27 (5), pages 1159–1168 (1979); and H. Stetter et al in the Journal of Heterocyclic Chemistry, 14, pages 573–581 (1977). 1-Phenylindolizine is disclosed by M. G. Reinecke et al in the Journal of Organic Chemistry, 31, pages 4215–4220 (1966). Octahydroindolizine compounds useful as analgesics are disclosed in our U.S. Pat. No. 4,582,836. I. Murakoshi discloses 3-phenylpyrrolizidine itself without mention of pharmaceutical activity in Yakugaku Zasshi, Vol. 78, p. 598–601 (1958). H. Faber et al. disclose 2-(3,4-dimethoxy)-3-(4-methoxyphenyl)pyrrolizidine in Helv. Chim. Acta, Vol. 56, p. 2882–2884 (1973).

SUMMARY OF THE INVENTION

Compounds of the present invention are of the following formula (I):

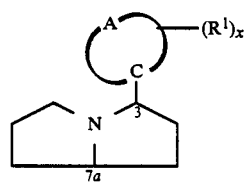

and acid addition salts wherein A represents the atoms necessary to form a 3 to 7 membered carbocyclic ring or a thienyl, furanyl, pyrrolyl, pyridinyl, pyridazinyl, pyrimidinyl, pyrazinyl or triazinyl ring, $R^1$ is a substituent and x is 0–3. Also included within the invention are pharmaceutical compositions, methods for the synthesis of formula (I) compounds and intermediates used in such synthesis.

DETAILED DESCRIPTION OF THE INVENTION

Compounds of the present invention are hexahydropyrrolizines of the following formula (I):

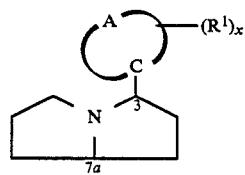

wherein

A represents the atoms necessary to form a ring system selected from the group consisting of phenyl, naphthyl, cycloalkyl, cycloalkenyl, thienyl, furanyl, pyrrolyl, pyridinyl, pyridazinyl, pyrimidinyl, pyrazinyl or triazinyl;

$R^1$ is independently cyano, halogen, alkyl, alkyloxy, alkylthio, haloalkyl, alkenyl, alkynyl or cycloalkenyl or $R^1$ is alkyl, alkenyl or alkynyl substituted by hydroxy; and x is the integer 0, 1, 2 or 3, provided that when A is phenyl, x is 1, 2 or 3, and the pharmaceutically-acceptable acid-addition salts thereof.

In more detail, A is phenyl; naphthyl; cycloalkyl of about 3 to 7 carbon such as cyclopentyl and cyclohexyl; cycloalkenyl of about 3 to 7 carbons such as cyclopentenyl and cyclohexenyl, e.g. 1-cyclohexen-1-yl; thienyl such as 2- or 3-thienyl; furanyl such as 2- or 3-furanyl; pyrrolyl such as 2- or 3-pyrrolyl; pyridinyl such as 2-, 3- or 4-pyridinyl; pyridazinyl such as 3- or 4-pyridazinyl; pyrimidinyl such as 2- 4- or 5-pyrimidinyl; pyrazinyl such as 2-pyrazinyl; or triazinyl such as 1, 2, 3-triazinyl attached at the 4 or 5 position thereof, 1, 2, 4-triazinyl attached at the 3, 5 or 6 position or 1, 3, 5-triazinyl attached at the 2 position.

$R^1$, in more detail, is independently, e.g., two different $R^1$ moieties may be attached to the A ring when x is 2, cyano; halogen such as fluoro, chloro, bromo and iodo; alkyl of about 1 to 8 carbons such as methyl, ethyl, n-propyl and sec-butyl; alkoxy of about 1 to 8 carbons such as methoxy, ethoxy and iso-propoxy; alkylthio of about 1 to 8 carbons such as methylthio and ethylthio; haloalkyl of about 1 to 8 carbons independently substituted by one or more of fluoro, chloro, bromo or iodo such as trifluoromethyl and 2,2,2-trifluoroethyl; alkenyl of about 2 to 8 carbons such as ethenyl, 1-propenyl and 2-propenyl; alkynyl of about 2 to 8 carbons such as ethynyl, 1-propargyl and 2-propargyl; cycloalkenyl of about 3 to 7 carbons such as cyclopropenyl and 1-cyclohexenyl; or such alkyl, alkenyl or alkynyl substituted by hydroxy such as 3-hydroxy-n-butyl, 3-hydroxy-1-n-butenyl and 6-hydroxy-1-n-hexynyl. Particular A-$R^1$ ring systems for formula (I) include phenyl rings where x is 0 or 1 and $R_1$ is halogen such as ortho-halophenyl, e.g., ortho-bromophenyl or $R_1$ is loweralkyl such as para-loweralkyl, e.g. para-methylphenyl.

Particular compounds of the invention include the following:

Hexahydro-3-phenyl-1H-pyrrolizine
3-(2-Bromophenyl)hexahydro-1H-pyrrolizine
Hexahydro-3-(4-methylphenyl)-1H-pyrrolizine Various isomers are possible in formula (I) compounds and the present invention includes all such individual enantiomers, diasteriomers, racemates and other isomer ratios. Specifically, formula (I) compounds have 3-substitution and, may exist in the following 4 forms, the pendant 7a bond being to a hydrogen:

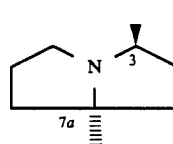

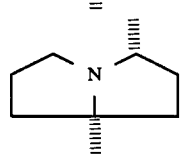

3
-continued

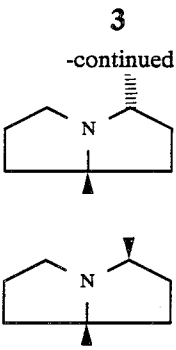

(Ic)

(Id)

Structures (Ia) and (Ic) are enantiomers of each other as are (b) and (d). In the present specification, the designation 3α, 7aβ in nomenclature of specific compounds is used for the pair (Ia) and (Ic) according to CA usage, it being clear that such 3α,7aα compound is a racemate composed of the 2 enantiomers (Ia) and (Ic). Likewise, 3α,7aα is the designation for the pair of compounds having partial structure (Ib) and (Id). Resolution of enantiomers shown in the application, of course, results in a single enantiomer without its enantiomeric mirror image and these individual enantiomers are designated by (−) or (+) according to the direction in which they turn polarized light.

Compounds of this invention may be prepared via either of two Routes (A) and (B).

Route (A)

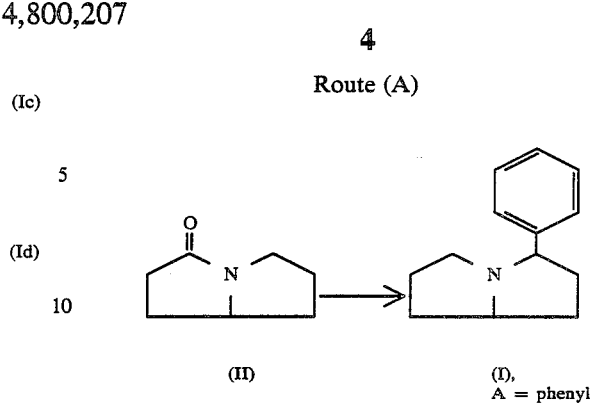

In Route (A), compounds of formula (I) wherein A is phenyl may be prepared by treatment of hexahydro-3H-pyrrolizin-3-one of formula (II) with phenyl lithium followed by dichloroaluminum hydride.

In more detail, hexahydro-3H-pyrrolizin-3-one, CA, Vol. 86, 89512 (1977), in a dry ethereal solvent, such as THF, is treated with a solution of about one equivalent of phenyllithium in cyclohexane/diethyl ether at a temperature below −20° C. After a period of about 1-2 hours, the reaction mixture is added to a suspension of about one equivalent of AlCl$_2$H in anhydrous ether. The reaction mixture is stirred at about room temperature for a period of about 16 to 24 hours under an inert atmosphere, e.g. nitrogen or argon, and the product of formula (I) wherein A is phenyl is recovered by standard techniques.

Route (B)

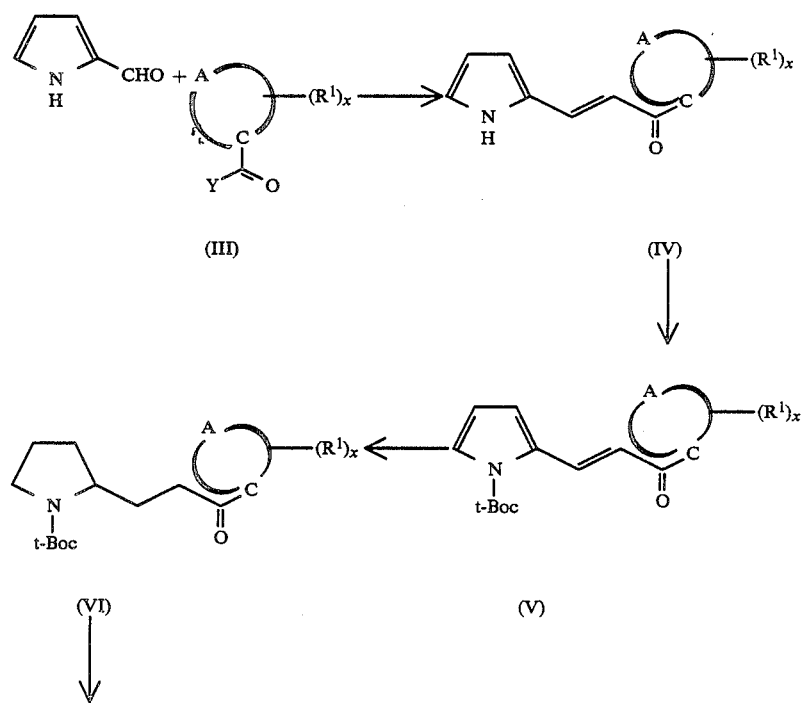

-continued

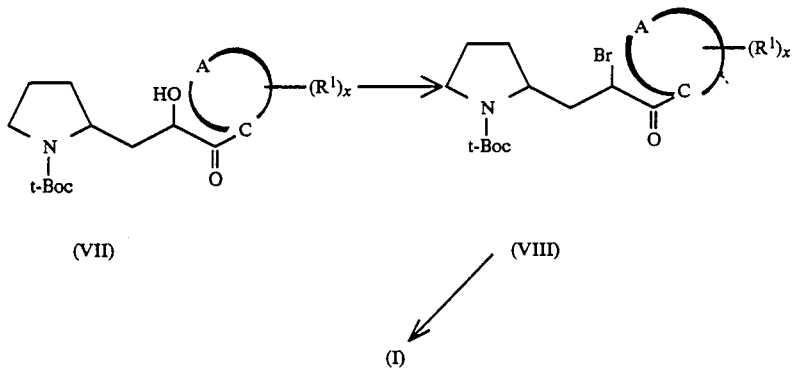

(VII)  (VIII)

(I)

In Route (B), pyrrole 2-carboxaldehyde is condensed with a ketone of formula (III) where Y is —CH$_3$, e.g. a substituted acetophenones or heteroaryl methyl ketone, to afford a chalcone of formula (IV). The condensation may be carried out under Claisen-Schmidt conditions, for instance, in water or a lower alcohol solvent at a temperature of −30° to 50° C., depending on the solvent being used, preferably water at about 45° C., in the presence of an alkali metal hydroxide, e.g. potassium hydroxide. Other alternative condensation procedures may be used, e.g. the Knoevenagel condensation using ammonia or a primary or secondary amine catalyst and a carboxylic acid. For instance, piperidine in acetic acid at an elevated temperature of about 50° to 100° C. will effect the condensation.

The chalcone of formula (IV) is then reacted with di-tert-butyldicarbonate to afford the t-Boc protected pyrrole chalcone of formula (V). The protection reaction is generally carried out in an inert solvent, e.g. acetonitrile, at room temperature.

The protected pyrrole chalcone of formula (V) is then catalytically hydrogenated to produce the pyrrolidine-ketone of formula (VI). The hydrogenation may be carried out over nickel or a noble metal catalyst, e.g. platinum, palladium, rhodium or ruthenium, preferably platinum or rhodium on carbon, in a solvent such as a lower alkenol, e.g. methol. The hydrogenation may be carried out at a temperature of about 20° to 120° C. at a hydrogen pressure of about 16 psi to 300 psi.

Route (B) is preferably not used if the A-ring constitutes a moiety which is sensitive to hydrogenation. Thus, Route (B) is best used when the A-ring is phenyl, naphthyl or furanyl.

In the next step of Route (B), the pyrrolidine-ketone of formula (VI) is reduced to produce a pyrrolidine-alcohol of formula (VII) by the action of a hydride reducing agent, e.g. sodium borohydride in a polar solvent, such as a lower alkanol, e.g. methanol, or LAH in Et$_2$O or THF. The pyrrolidine-alcohol of formula (VII) is then treated with aqueous concentrated hydrogen bromide to produce the N-deprotected pyrrolidinehalide hydrobromide of formula (VIII). The deprotection of the pyrrolidine nitrogen and conversion of the alcohol moiety to a bromine moiety is carried out in a single step at an elevated temperature of about 38° to 100° C., preferably about 60° C.

In the last step of Route (B), the pyrrolidinehalide hydrobromide of formula (VIII) is cyclized to a hexahydropyrrolizine of formula (I) by conversion of the hydrobromide salt to its free base and subsequent cyclization of the free base. The reaction is carried out by the action of a mild base 1 e.g. potassium carbonate, in a polar solvent, e.g. water.

Route (B) may not be employed when the group

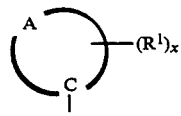

contains a group subject to a catalytic hydrogenation such as a C-C double bond, a C-C triple bond, a nitrile, a pyridine ring or a thiophene ring.

When the A-C cycle is a phenyl ring, carrying out Route (B) with exhaustive Rh catalyzed hydrogenation affords a 3-cyclohexylhexahydropyrrolizine. In a variation of Route (B), the protected pyrrolidine alcohol of formula (VII) is reacted with thionyl chloride in place of concentrated hydrogen bromide to produce an N-deprotected chloro pyrrolidine hydrochloride analogous to the bromo pyrrolidine of formula (VIII) of Route (B), which is subsequently cyclized to a hexahydropyrrolizine of formula (I) by the action of a strong base. The thionyl chloride reaction is generally run in a polar aprotic solvent, e.g. chloroform, at room temperature and the strong base used in the cyclization step is aqueous alkali, e.g. sodium hydroxide. In each of Route (A) and (B), a mixture of diastereomers is produced. The diastereomers may be separated by chromatography on silica or by fractional crystallization. If desired, the compound of formula (I) may be resolved into optical isomers, i.e., enantiomers, by fractional crystallization of a salt with an optionally active acid such as, for instance, di-p-toluoyl tartaric acid.

The groups R$^1$ may be attached directly to the —C-A function during the synthesis of the hexahydropyrrolizine ring. Alternatively they may be attached following the synthesis of the 3-substituted hexahydropyrrolizine. For instance a 3-(halophenyl)hexahydropyrrolizine may be converted to the corresponding lithium derivative by reaction with an alkyllithium. 3-(2-Lithiophenyl)hexahydropyrrolizine on reaction with dimethyldisulfide affords 3-(2-methylthiophenyl)hexahydropyrrolizine. Reaction of the lithio derivative with cyclohexanone affords the derivative with a 1-cyclohexanol attached. A 3-(2-halophenyl)hexahydropyrrolizine when subjected to palladium catalyzed coupling with cuprous cyanide or a 1-alkyne gives the corresponding cyano or alkyl derivative.

Compounds of formula (I) wherein the A-ring is cyclohexyl or substituted cyclohexyl may be prepared by catalytic hydrogenation of the appropriate phenyl compound over a noble metal catalyst, for example rhodium, ruthenium or platinum.

The activity of compounds of the invention as analgesics may be demonstrated by an abdominal constriction assay as described below:

Mouse Acetylcholine-Bromide-Induced Abdominal Constriction Assay

The mouse acetylcholine-induced abdominal constriction assay, as described by Collier et al. in Brit. J. Pharmacol. Chemother, 32: 295–310, 1968, with minor modifications was one test used to assess analgesic potency. The test drugs or appropriate vehicle were administered p.o. and 30 minutes later the animals received an i.p. injection of 5.5 mg/kg acetylcholine bromide (Matheson, Coleman and Bell, East Rutherford, N.J.). The mice where then placed in groups of four into glass bell jars and observed for a ten minute observation period for the occurrence of a writhe which is defined as a wave of constriction and elongation passing caudally along the abdominal wall, accompanied by a twisting of the trunk and followed by extension of the hind limbs. The percent inhibition of writhing (equated to % analgesia) was calculated as follows: The % inhibition of writhing, i.e., % analgesia is equal to the difference between the number of control animals writhing and the number of drug-treated animals writhing times 100 divided by the number of control animals writhing.

At least 20 animals were used for control and in each of the drug treated groups. Four doses were used to determine each dose response curve and $ED_{50}$ (that dose which inhibits writhing by 50%). The $ED_{50}$ values and their 95% fiducial limits were determined by a computer assisted probit analysis. The test results are shown in Table I.

TABLE I

| Acetyl Choline Bromide Body Constriction | | |
|---|---|---|
| Cpd of Ex # | % Inhibition 30 mg Kg | $ED_{50}$ |
| 1 | 100 | 5.7 |
| 2f (diasteriomer A) | 60 | — |
| 2f (diasteriomer B) | 100 | 8.7 |
| 3d | 100 | — |

Based on the above results, compounds of the invention as well as the compound of formula (I) where A is phenyl and x is 0 may be used to treat mild to moderately severe pain in warm blooded animals such as humans in a manner similar to the use of meperidine hydrochloride by administration of an analgesically effective dose. The dosage range would be from about 10 to 3000 mg, in particular about 25 to 1000 mg or about 100 to 500 mg, of active ingredient 1 to 4 times per day for an average (70 kg) human although it is apparent that activity of individual compounds of the invention will vary as will the pain being treated.

To prepare the pharmaceutical compositions of this invention, one or more compounds or salt thereof of the invention as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., table, capsule, powder, injection, teaspoonful and the like, from about 10 to about 500 mg of the active ingredient.

In the following Examples and throughout the specification, the following abbreviations may be used: CA (Chemical Abstracts); mg (milligrams); g (grams); kg (kilograms); mL (milliliters); mmole (milli moles); M (molar); N (normal); psi (pounds per square inch); mp (melting point); bp (boiling point); meg (milliequivalents); E (trans); Z (cis); $Et_2O$ (diethyl ether); EtOAc (ethyl acetate); MeOH (methanol); EtOH (ethanol); LAH (lithium aluminum hydride); THF (tetrahydrofuran); DMF (dimethylformamide); p.o. (per os, orally); i.p. (intraperitioneal); hplc (high pressure liquid chromatography; hr (hours); min (minutes); and C,H,N,O, etc. (the chemical symbols for the elements). Unless otherwise indicated, all temperatures are reported in °C. (degrees centigrade) and all references to ether are to $Et_2O$.

EXAMPLE 1

Hexahydro-3-phenyl-1H-pyrrolizine

Into a round bottom flask was placed 5 g (0.04 moles) hexahydro-3H-pyrrolizin-3-one, described in CA, 86 89512 (1977) in 100 mL of dry THF. This was cooled to −40° C. and 20 mL of 2.0M phenyllithium in cyclohexane/ether was added over 40 min keeping the temperature below −20° C. The reaction mixture was stirred at −20° C. for 40 min and added to a suspension of $AlCl_2H$ made by adding 5.34 g (0.04 moles) aluminum chloride in 25 mL of dry ether to a suspension of 1.52 g (0.04 moles) LAH in ether. The reaction mixture was stirred overnight under nitrogen. To the reaction mixture was added 120 mL of water and it was stirred for one hr. The solid was filtered off and washed well with ether. The filtrate was made basic with 3N sodium hydroxide and extracted several times with ether. The ether layers were combined, washed with brine and dried ($K_2CO_3$). The solvent was removed in vacuo. The residue was taken up in ether, washed with water and extracted with 3N hydrogen chloride. The acidic layer was made basic by sodium hydroxide addition and extracted with ether. The ether layer was washed with brine, dried ($K_2CO_3$) and the solvent evaporated in vacuo. The resulting oil was flashed chromatographed on silica gel using 1:7 acetone:hexane as the eluant. The resulting oil was treated with one equivalent of fumaric acid in 2-propanol to give the salt which was recrystallized from 2-propanol to give 680 mg of hexahydro-3-phenyl-1H-pyrrolizine (E)-2-butenedioate (9%), mp 143°–145.5° C.

EXAMPLE 2 a. 1-(2-Bromophenyl)-3-(1H-pyrrol-2-yl)-2-propen-1-one

A mixture of 20.0 g of (0.21 moles) 2-pyrrolecarboxaldehyde, 71.4 mL of (0.52 moles) o-bromoacetophenone, 72 mL of 1N potassium hydroxide and 800 mL of water was placed in a flask under nitrogen and heated to 45° C. for 72 hr. The reaction was cooled in an ice bath until a solid formed. The solid was taken up in methylcyclohexane/EtOAc, dried over 4A sieves and allowed to cool. The resulting solid was recrystallized from methylcyclohexane/EtOAc to give 43.5 g of 1-(2-bromophenyl)-3-(1H-pyrrol-2-yl)-2-propen-1-one as a yellow solid (75%), mp 76°–78° C.

b. 1,1-Dimethylethyl 2-[3-(2-bromophenyl)-3-oxo-1-propenyl]-1H-pyrrol-1H-pyrrol-1-carboxylate To a solution of 27.7 g (0.10 moles) 1-(2-bromophenyl)-3-(1H-pyrrol-2-yl)-2-propen-1-one in 120 mL of acetonitrile was added 26.16 g (0.12 moles) of di-t-butyldicarbonate and 1.27 g (0.01 moles) of dimethylaminopyridine. The solution was stirred for 45 min after which 3.54 g (0.03 moles) of 2-diethylaminoethylamine was added. After stirring for 15 min the reaction was partitioned between 200 mL of 1M potassium hydrogen sulfate and ether. The ether layer was washed twice with 100 mL portions of 1M potassium hydrogen sulfate, water brine and dried ($K_2CO_3$). Evaporation of the solvent in vacuo gave 34.4 g of 1,1-dimethylethyl 2-[3-(2-bromophenyl)-3-oxo-1-propenyl]-1H-pyrrol-1-carboxylate as an oil (92%).

c. 1,1-dimethylethyl 2-[3-(2-bromophenyl)-3-oxo-propyl]-1H-pyrrolidine-1-carboxylate Into a Parr shaker bottle was placed a solution of 37.47 g (0.099 moles) 1,1-dimethylethyl 2-[3-(2-bromophenyl)-3-oxo-1-propenyl]-1H-pyrrol-1-carboxylate in 150 mL of methyl alcohol and 1.90 g of Platinum oxide. The reaction was placed under a 60 psi atmosphere of hydrogen and shaken until hydrogen uptake had stopped. The catalyst was filtered off and the filtrate was evaporated in vacuo to give 32.9 g of 1,1-dimethylethyl 2-[3-(2-bromophenyl)-3-oxopropyl]-1H-]-pyrrolidine-1-carboxylate as a yellow oil (86%).

d. 1,1-dimethylethyl 2-[3-(2-bromophenyl)-3-hydroxypropyl]-1H-pyrrolidine-1-carboxylate To a solution of 20.0 g (0.052 moles) of 1,1-dimethylethyl 2-[3-(2-bromophenyl)-3-oxopropyl]-1H-pyrrolidine-1-carboxylate in 100 mL of methyl alcohol placed under an atmosphere of nitrogen was added portionwise 3.10 g (0.09 moles) of sodium borohydride pellets. After stirring overnight water was added and the methanol was evaporated in vacuo. The residue was partitioned between ether and water, and the ether layer was washed with brine and dried ($K_2CO_3$). Evaporation of the solvent in vacuo gave 19.42 g of 1,1-dimethylethyl 2-[3-(2-bromophenyl)-3-hydroxypropyl]-1H-pyrrolidine-1-carboxylate as a brown oil (97%).

e. 2-[3-bromo-3-(2-bromophenyl)propyl]pyrrolidine hydrobromide

To 550 mL of 48% hydrogen bromide was added 22.03 g (0.057 moles) of 1,1-dimethylethyl2-[3-(2-bromophenyl)-3-hydroxypropyl]-1H-pyrrolidine-1-carboxylate. The solution was heated to 60° C. for 30 min, placed in a freezer to cool and after five hr a solid was collected. The filtrate was evaporated in vacuo and a solution of 5% water in 2-propanol was added to the residue. After sitting in a freezer overnight, a solid was filtered which was identical to the first solid isolated. A total of 9.7 g of 2-[3-bromo-3-(2-bromophenyl)propyl]pyrrolidine hydrobromide was collected (40%), mp 169°–170° C.

f. 3-(2-bromophenyl)hexahydro-1H-pyrrolizine

To 100 mL of chloroform was added 10.21 g (0.024 moles) of 2-[3-bromo-3-(2-bromophenyl)propyl]pyrrolidine hydrobromide and a solution of 6.6 g (0.048 moles) potassium carbonate in 25 mL of water. The reaction mixture was stirred vigorously for four hr. The organics were separated off, washed with water, brine and dried ($K_2CO_3$). The solvent was evaporated in vacuo to give 5.41 g of two diastereomers of 3-(2-bromophenyl)hexahydro-1H-pyrrolizine (diastereomer A and diastereomer B). The diastereomers were separated by flash chromatography on silica gel using 1:5 acetone:hexane as the eluant. The first diastereomer to elute from the column, diastereomer A, was treated with a solution of hydrogen chloride in ether to give 460 mg of diastereomer A hydrochloride (6.3%), mp 154°–157° C. Diastereomer B was distilled in a Kugelrohr collecting the distillate between 120°–130° C. at 0.01 mm Hg. A 1.0 g sample of diastereomer B was collected as a clear oil (16%).

EXAMPLE 3 a. 1-(4-methylphenyl)-3-(2-pyrrolyl)-2-propen-1-one

To a solution of 10.1 g (0.18 mole) of potassium hydroxide in 2.18 L of water was added 176.4 g (1.32 mole) of 4-methylacetophenone and 50 g (0.53 mole) of pyrrole-2-carboxaldehyde. The mixture was heated to 40°–45° C. with mechanical stirring under a nitrogen atmosphere overnight. The solid precipitate was filtered, washed with water and 2-propanol, and air dried to give 42.1 g (38% yield) of the title compound as a solid, mp 158.5°–159.5° C.

b. 1,1-Dimethylethyl 2-[3-(4-methylphenyl)-3-oxo-1-propenyl]-1H-pyrrole-1-carboxylate To a suspension of 42.1 g (0.2 mole) of the product of Example 3a in 400 mL of acetonitrile was added 1.95 g (0.16 mole) of 4-dimethylaminopyridine and 52.3 g (0.24 mole) of di-t-butyldicarbonate. The solution was allowed to stir at room temperature overnight. The reaction was poured into 1.3 L of 1N potassium bisulfate and extracted with ether. The ether solution was dried over anhydrous potassium carbonate and concentrated to give 61.4 g (98% yield) of the title compound as a dark yellow oil which solidified on scratching.

c. 1,1-Dimethylethyl 2-[3-hydroxy-3-(4-methylphenyl)propyl]-1H-pyrrole-1-carboxylate To a solution of 61 g (0.196 mole) of the product of Example 3b in 300 mL of absolute methanol was added 2.4 g of platinum oxide and the mixture was placed on a Parr apparatus under 60 psi of hydrogen and shaken for 3 days. The mixture was filtered and the filtrate concentrated to give 56.5 g (90% yield) of the title compound as a brown oil.

d. Hexahydro-3-(4-methylphenyl)-1H-pyrrolizine

To a solution of 51.8 g (0.162 mole) of the product of Example 3c in 500 ml of dry chloroform was added 23.6 ml (0.32 mole) of thionyl chloride dropwise with mechanical stirring. The mixture was allowed to stir for 2 hr at ambient temperature, basified with 3N sodium hydroxide and stirred overnight. The chloroform layer was separated, dried over anhydrous potassium carbonate, and concentrated to an oil. The oil was chromatographed on silica, eluting with 50% acetone:hexane and the product bearing fractions were combined to give 7.5 g of an oil. This oil was distilled, and the fraction boiling at 80°–82° C./0.1 Torr was treated with ethereal HCl to give the salt which was recrystallized from acetonitrile to give 2.8 g (5% yield) of the title compound as a tan solid, mp 199.5°–203.5° C.

What is claimed is:

1. A hexahydropyrrolizine of the following formula (I):

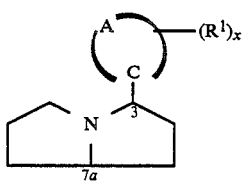

(I)

wherein
A represents the atoms necessary to form a phenyl, naphthyl, cycloalkyl of 3 to 7 carbons, cycloalkenyl of 3 to 7 carbons, thienyl, furanyl or pyrrolyl ring system as the A-C cycle shown in formula (I);
$R^1$ is independently cyano, halogen, alkyl of 1 to 8 carbons, alkyloxy of 1 to 8 carbons, alkylthio of 1 to 8 carbons, haloalkyl of about 1 to 8 carbons, alkenyl of 2 to 8 carbons, alkynyl of 2 to 8 carbons, cycloalkenyl of 3 to 7 carbons or such an alkyl, alkenyl or alkynyl substituted by hydroxy; and
x is the integer 0, 1, 2, or 3,
provided that when A represents a phenyl ring, x is 1, 2 or 3, or a pharmaceutically-acceptable acid-addition salt thereof.

2. The hexahydropyrrolizine of claim 1, wherein the hydrogen atoms at the 3 and 7a positions of formula (I) are cis to each other.

3. The hexahydropyrrolizine of claim 2, wherein the hydrogen atoms at the 3 and 7a positions of formula (I) are alpha hydrogens.

4. The hexahydropyrrolizine of claim 2, wherein the hydrogen atoms at the 3 and 7a positions of formula (I) are beta hydrogens.

5. The hexahydropyrrolizine of claim 1, wherein the hydrogen atoms at the 3 and 7a positions of formula (I) are trans to each other.

6. The hexahydropyrrolizine of claim 1, wherein A represents the atoms necessary to form a phenyl ring.

7. The hexahydropyrrolizine of claim 6, wherein x is 1, 2 or 3 and at least one $R^1$ group is at the ortho position of the phenyl ring.

8. The hexahydropyrrolizine of claim 7, wherein x is 1 and the $R^1$ group is at the ortho position of the phenyl ring.

9. The hexahydropyrrolizine of claim 1, wherein said hexahydropyrrolizine is selected from the group consisting of:
3-(2-bromophenyl)hexahydro-1H-pyrrolizine, and
hexahydro-3-(4-methylphenyl)-1H-pyrrolizine,
or a pharmaceutically-acceptable acid-addition salt thereof.

10. The hexahydropyrrolizine of claim 9, which is the $3\alpha 7a\beta$ pair of enantiomers.

11. A pharmaceutical composition effective in the treatment of pain which comprises a pharmaceutically-acceptable carrier and a pain-reducing amount of a hexahydropyrrolizine of the following formula (I):

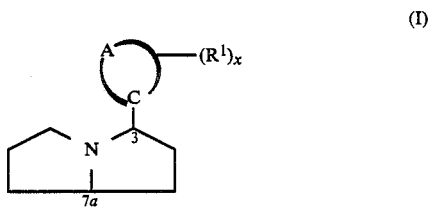

(I)

wherein
A represents the atoms necessary to form a phenyl, naphthyl, cycloalkyl of 3 to 7 carbons, cycloalkenyl of 3 to 7 carbons, thienyl, furanyl or pyrrolyl ring system as the A-C cycle shown in formula (I);
$R^1$ is independently cyano, halogen, alkyl of 1 to 8 carbons, alkyloxy of 1 to 8 carbons, alkylthio of 1 to 8 carbons, haloalkyl of 1 to 8 carbons, alkenyl of 2 to 8 carbons, alkynyl of 2 to 8 carbons, cycloalkenyl of 3 to 7 carbons or such an alkyl, alkenyl or alkynyl substituted by hydroxy; and
x is the integer 0, 1, 2, or 3,
or a pharmaceutically-acceptable acid-addition salt thereof.

12. The pharmaceutical composition of claim 11 wherein said hexahydropyrrolizine is selected from the group consisting of:
hexahydro-3-phenyl-1H-pyrrolizine,
3-(2-bromophenyl)hexahydro-1H-pyrrolizine, and
hexahydro-3-(4-methylphenyl)-1H-pyrrolizine,
or a pharmaceutically-acceptable acid-addition salt thereof.

13. A method of relieving pain in a mammal which comprises administering to the mammal an effective amount of a pharmaceutical composition of claim 11.

14. The method of claim 13, wherein said mammal is a human.

15. The method of claim 13 wherein said hexahydropyrrolizine is selected from the group consisting of:
hexahydro-3-phenyl-1H-pyrrolizine,
3-(2-bromophenyl)hexahydro-1H-pyrrolizine, and
hexahydro-3-(4-methylphenyl)-1H-pyrrolizine,
or a pharmaceutically-acceptable acid-addition salt thereof.

* * * * *